United States Patent [19]

Miller

[11] Patent Number: 5,374,524
[45] Date of Patent: Dec. 20, 1994

[54] SOLUTION SANDWICH HYBRIDIZATION, CAPTURE AND DETECTION OF AMPLIFIED NUCLEIC ACIDS

[75] Inventor: Jeffrey A. Miller, Derry, N.H.

[73] Assignee: E. I. Du Pont de Nemours and Company, Wilmington, Del.

[21] Appl. No.: 53,842

[22] Filed: Apr. 27, 1993

Related U.S. Application Data

[63] Continuation of Ser. No. 478,297, Feb. 9, 1990, abandoned, which is a continuation-in-part of Ser. No. 192,090, May 10, 1988, abandoned.

[51] Int. Cl.$^5$ .................... C12Q 1/68; C12P 19/34
[52] U.S. Cl. ............................... 435/6; 435/91.2; 435/810; 436/501; 536/22.1; 536/24.3; 935/77; 935/78; 935/88
[58] Field of Search ............... 435/6, 810, 91, 91.1, 435/91.2; 436/501; 536/27.1, 23.1, 24.1–24.33; 935/77, 78, 88

[56] References Cited

U.S. PATENT DOCUMENTS

| | | | |
|---|---|---|---|
| Re. 31,006 | 8/1982 | Schuurs et al. | 435/7 |
| 2,785,057 | 3/1957 | Schwab et al. | 23/253 |
| 3,011,874 | 12/1961 | Deutsch | 23/253 |
| 3,232,710 | 2/1966 | Rieckmann et al. | 23/253 |
| 3,249,513 | 5/1966 | Babson | 195/66 |
| 3,341,427 | 9/1967 | Evans et al. | 195/103.5 |
| 3,420,205 | 1/1969 | Morison | 116/114 |
| 3,482,943 | 12/1969 | Csizmas et al. | 23/253 |
| 3,511,608 | 5/1970 | Anderson | 23/253 |
| 3,620,677 | 11/1971 | Morison | 23/253 |
| 3,663,374 | 5/1972 | Moyer et al. | 195/103.5 R |
| 3,715,192 | 2/1973 | Wenz et al. | 23/253 TP |
| 3,723,064 | 3/1973 | Liotta | 23/230 R |
| 3,783,105 | 1/1974 | Moyer et al. | 195/127 |
| 3,791,933 | 2/1974 | Moyer et al. | 195/127 |
| 3,802,842 | 4/1974 | Lange et al. | 23/253 TP |
| 3,888,629 | 6/1975 | Bagshawe | 23/230 B |
| 3,896,217 | 7/1975 | Johnson | 424/1 |
| 3,901,657 | 8/1975 | Lightfoot | 23/253 TP |
| 4,087,248 | 5/1978 | Miles | 23/230 B |
| 4,092,115 | 5/1978 | Rupe et al. | 23/230 R |
| 4,098,876 | 7/1978 | Piasio et al. | 424/1 |
| 4,200,690 | 4/1980 | Root et al. | 435/7 |
| 4,201,763 | 5/1980 | Monthony et al. | 424/8 |
| 4,235,601 | 11/1980 | Deutsch et al. | 23/230 R |
| 4,244,940 | 1/1981 | Jeong et al. | 424/1 |
| 4,246,339 | 1/1981 | Cole et al. | 435/7 |
| 4,258,001 | 3/1981 | Pierce et al. | 422/56 |
| 4,277,560 | 7/1981 | Gray et al. | 435/7 |
| 4,361,537 | 11/1982 | Deutsch et al. | 422/56 |
| 4,362,901 | 12/1982 | Valkirs et al. | 435/5 |
| 4,366,241 | 12/1982 | Tom et al. | 435/7 |
| 4,391,904 | 7/1983 | Litman et al. | 435/7 |
| 4,407,943 | 10/1983 | Cole et al. | 435/7 |
| 4,472,498 | 9/1984 | Masuda et al. | 435/7 |
| 4,512,896 | 4/1985 | Gershoni | 210/635 |
| 4,549,655 | 10/1985 | Forsythe, Jr. et al. | 206/569 |
| 4,581,331 | 4/1986 | Richards et al. | 435/4 |
| 4,623,461 | 11/1986 | Hossom et al. | 210/445 |
| 4,652,533 | 3/1987 | Jolley | 436/518 |
| 4,683,195 | 7/1987 | Mullis et al. | 435/6 |
| 4,708,932 | 11/1987 | Axén et al. | 435/7 |
| 4,748,115 | 5/1988 | Steaffens | 435/21 |
| 4,751,177 | 6/1988 | Stabinsky | 435/6 |
| 4,818,677 | 4/1989 | Kaufman et al. | 435/4 |
| 4,828,980 | 5/1989 | Snyder et al. | 435/7 |
| 4,849,505 | 7/1989 | Stavrianopoulos | 530/300 |
| 4,894,325 | 1/1990 | Englehardt et al. | 435/6 |
| 5,006,464 | 4/1991 | Chu et al. | 435/7.1 |
| 5,137,804 | 8/1992 | Greene et al. | 435/5 |

FOREIGN PATENT DOCUMENTS

0200381 11/1986 European Pat. Off. .

(List continued on next page.)

OTHER PUBLICATIONS

Syvanen et al. (1986) Nucleic Acids Res., vol. 14, No. 12, pp. 5037–5048.

(List continued on next page.)

*Primary Examiner*—Margaret Parr
*Assistant Examiner*—Ardin H. Marschel

[57] ABSTRACT

A nucleic acid probe assay which combines nucleic acid amplification with solution hybridization using capture and reporter probes followed by or simultaneously with immobilization on a solid support is provided. An assay sensitivity equal to 5 copies of HIV I DNA was achieved.

1 Claim, No Drawings

FOREIGN PATENT DOCUMENTS

| | | |
|---|---|---|
| 0239222 | 9/1987 | European Pat. Off. . |
| 1348938 | 3/1974 | United Kingdom . |
| 1401297 | 7/1975 | United Kingdom . |
| 1401298 | 7/1975 | United Kingdom . |
| 1420916 | 1/1976 | United Kingdom . |
| 2001172A | 1/1979 | United Kingdom . |
| 2008767A | 6/1979 | United Kingdom . |
| 2018986A | 10/1979 | United Kingdom . |
| 1564578 | 4/1980 | United Kingdom . |

OTHER PUBLICATIONS

Ratner et al. (1985) Nature, vol. 313, pp. 277–284.

Matthews et al. (1988) Analytical Biochemistry, vol. 169, pp. 1–25.

Karjalainen et al. (1987) J. of Agric. Sci in Finland, vol. 59, pp. 179–191.

Greene et al., "A Rapid Membrane-Based Diagnostic Test for Detection of Herpes Simplex Virus", 1988 *ASM Annual Meeting* (8–13 May), p. VII, Abstract.

Millipore Immunozyme Toxoplasma Antibody Test, No. PD847 (1979).

Litman et al., Clin. Chem., pp. 1598–1603, vol. 29, No. 9 (1983).

Kwock et al., "Identification of Human Immunodeficiency Virus Sequences . . . ", Journal of Virology, May 1987, pp. 1690–1694.

Erlich et al., "Specific DNA Amplification", Nature, vol. 331, 4 Feb. 1988, pp. 461–462.

Biosis Abstract: 85085381. Karjalainen et al., "Diagnosis of Plant Virus by Nucleic Acid Hybridization".

Ratner et al. (1987) AIDS Research and Human Retroviruses, vol. 3, No. 1, pp. 57–69.

Abstract of Karjalainen, R. et al. (1987) J. Agric. Sci. (Finl) vol. 59(3) pp. 179–192.

SOLUTION SANDWICH HYBRIDIZATION, CAPTURE AND DETECTION OF AMPLIFIED NUCLEIC ACIDS

This is a continuation of application Ser. No. 07/478,297 filed Feb. 9, 1990, now abandoned, itself a continuation-in-part, of application Ser. No. 07/192,090 filed May 10, 1988, now abandoned.

FIELD OF INVENTION

This invention relates to nucleic acid hybridization for the detection of nucleic acid sequences and more specifically to a process of combining amplification of target nucleotide sequences with solution sandwich hybridization of the amplified target material.

BACKGROUND OF THE INVENTION

The development of practical nucleic acid hybridization methods which can be used for detecting nucleic acid sequences of interest has been limited by several factors. These include lack of sensitivity, complexity of procedure, and the desire to convert from radiometric to nonradiometric detection methods. A variety of methods have been investigated for the purpose of increasing the sensitivity of nonradiometric procedures. In one general approach, improvements in the total assay procedure have been examined, with concomitant effects on the issues of complexity and nonradiometric detection. In another approach, methods which increase the amount of nucleic acid to be detected by such assays have been pursued.

U.S. Pat. No. 4,358,535, issued to Falkow, describes a method of culturing cells to increase their number and thus the amount of nucleic acid of the organism suspected to be present, depositing the sample onto a fixed support, and then contacting the sample with a labeled probe, followed by washing the support and detecting the label. One drawback to this method is that without culturing the organism first, the assay does not have adequate sensitivity. Adding a culture step, however, is time consuming and not always successful. Maniatis et al., *Molecular Cloning: A Laboratory Manual*, Cold Spring Harbor Laboratory, pp. 390–401 (1982), describe a method in which a nucleic acid of interest is amplified by cloning it into an appropriate host system. Then, when the host organism replicates in culture, the nucleic acid of interest is also replicated. This method also suffers from the requirement to perform a culture step and thus provides for a procedure that is time consuming and complicated.

An alternative approach to increasing the quantity of nucleic acids of organisms has been described in U.S. Pat. Nos. 4,683,202 and 4,683,195. These patents disclose "a process for amplification and detection of any target nucleic acid sequence contained in a nucleic acid or mixture thereof". This process employs an in vitro cycling mechanism which doubles the nucleic acid sequence to be amplified after each cycle is complete. This is carried out by separating the complementary strands of the nucleic acid sequence to be amplified, contacting these strands with excess oligonucleotide primers and extending the primers by enzymatic treatment to form primer extension products that are complementary to the nucleic acid annealed with each primer. The process is then repeated as many times as is necessary. An advantage of this method is that it can rapidly produce large quantities of a small portion of the sequence of the nucleic acid of an organism of interest. A disadvantage of this method is that the detection of the nucleic acids produced, using a direct assay method, is complicated in that the amplification process can produce nucleic acid sequences which are not faithful copies of the original nucleic acid which was to be copied. These erroneous nucleic acid sequences can provide false positives in the assay which increase the background noise and thus decrease the sensitivity of the entire method.

Numerous DNA probe assays have been described in the past for the detection of nucleic acids of interest. Falkow's method (above) first renders the target nucleic acid single-stranded and then immobilizes it onto a solid support. A labeled probe which is complementary to the target nucleic acid is then brought into contact with the solid support. Any excess probe is washed away and the presence of the label in the resulting hybrid is determined. A disadvantage of this method is that it is time consuming and cumbersome. The assay steps, i.e., hybridization and washing steps are carried out in a sealed pouch which contains the membrane (solid support) as well as the buffer solution.

Hill et al., WO 86/05815, describe a variation of the above assay format employing nitrocellulose coated magnetic particles to which the target DNA is affixed, followed by direct hybridization with a biotinylated probe and detection using a streptavidin-conjugated reporter.

Dunn et al., *Cell*, Vol. 12, 23–36 (1977), describe a different hybridization format which employs a two-step sandwich assay method employing polynucleotide probes in which the target nucleic acid is mixed with a solution containing a first or capture probe which has been affixed to a solid support. After a period of time, the support is washed and a second or reporter (labeled) probe, also complementary to the target nucleic acid but not to the capture probe, is added and allowed to hybridize with the capture probe—target nucleic acid complex. After washing to remove any unhybridized reporter probe, the presence of the reporter probe, hybridized to the target nucleic acid, is detected.

Ranki et al. U.S. Pat. No. 4,563,419, disclose EPA 0 154 505, WO86/03782, and EPA 0 200 113. It is to be recognized that all of these employ an assay procedure in which the first or capture probe is immobilized onto a solid support prior to hybridization.

A further variation has been described in German Preliminary Published Application 3,546,312 A1. This method, like that described by Ranki et al., employs a capture probe and a reporter probe which hybridize to distinct portions of the target nucleic acid. The target nucleic acid is contacted in solution by the two probes. The first, or capture probe, contains a binding component, such as biotin, that is capable of binding with a receptor component, such as streptavidin, which has been affixed to a solid support. After formation of the capture probe—target nucleic acid—reporter probe complex, a streptavidin-modified solid support is added. Any unhybridized reporter probe is washed away followed by the detection of the label incorporated into the complex bound to the solid support. An advantage of this technique over that disclosed by Ranki et al. is that the hybridization, which takes place in solution, is favored kinetically. Some disadvantages are that the length of the target nucleic acid affects the overall efficiency of the reaction which decreases with increasing target nucleic acid length. Also, sandwich nucleicacid probe assays, whether heterogeneous two-step or one-step, or utilizing solution hybridization, are not as sensitive as the direct assay method.

DISCLOSURE OF THE INVENTION

The nucleic acid probe assay of this invention for the detection and/or measurement of a preselected nucleic acid sequence in a sample suspected of including a nucleic acid containing said preselected sequence comprises the steps of:

(A) rendering the target nucleic acid single-stranded;
(B) amplifying at least one specific nucleic acid sequence contained within the preselected nucleic acid sequence by
  (1) treating the strands with two oligonucleotide primers, for each different specific sequence being amplified, under conditions such that for each different sequence being amplified an extension product of each primer is synthesized which is complementary to each nucleic acid strand, wherein said primers are selected so as to be sufficiently complementary to the different strands of each specific sequence to hybridize therewith such that the extension product synthesized from one primer, when it is separated from its complement, can serve as a template for synthesis of the extension product of the other primer;
  (2) separating the primer extension products from the templates on which they were synthesized to produce single-stranded molecules; and
  (3) treating the single-stranded molecules generated from step (2) with the primers of step (1) under conditions that a primer extension product is synthesized using each of the single strands produced in step (2) as a template;
  (4) repeating steps (2) and (3) to produce sufficient primer extension product for detection and/or measurement;
(C) rendering the product of step (B) (4) single-stranded;
(D) contacting the product of step (C) with capture and reporter probes in solution wherein said capture probe is complementary to a portion of a primer extension product not including the nucleic acid sequences defined by both primers; wherein said reporter probe is complementary to a portion of a primer extension product not including the nucleic acid sequences defined by the capture probe and by both primers; and wherein the capture and reporter probes are complementary to the same nucleic acid strand;
(E) immobilizing the sandwich product of step (D) by contacting it with a solid support having an anchor receptor group on its surface capable of interacting with the anchor group of the capture probe;
(F) removing any unhybridized reporter probe; and
(G) detecting and/or measuring the reporter group immobilized on the solid support.

The assay of this invention can also comprise assay steps wherein, in step (D) above, the product of step (C) is contacted simultaneously with capture and reporter probes in solution and with a solid support having an anchor receptor group on its surface allowing the immobilization of a sandwich product formed in this step.

DETAILED DESCRIPTION OF THE INVENTION

The nucleic acid probe assay of this invention comprises the following overall process for the detection of target nucleic acids of a preselected sequence:

a) Using the polymerase chain reaction (PCR) nucleic acid amplification method described in U.S. Pat. No. 4,683,202, incorporated herein by reference, specific nucleic acid sequences are amplified by annealing the denatured target nucleic acid present in the sample with primers specific for the target and forming extension products. Each extension product formed is complementary to a portion of the preselected nucleic acid sequence contained within the target nucleic acid and becomes a template for further primer binding. This process is then repeated as necessary in order to produce the desired amount of primer extension product for detection and/or measurement.

b) The resulting nucleic acid is rendered single-stranded by known methods, such as treatment with heat, chaotropic agents, or by raising or lowering the pH. The single-stranded nucleic acid so produced is then contacted, simultaneously or sequentially, with buffered solutions containing nucleic acid capture and reporter probes, respectively. The first probe, designated the capture probe, is an oligonucleotide (nucleic acid) sequence, which is complementary to a portion of the target nucleic acid, but not to the primer utilized in the amplification step, to which is attached a functional group designated as the anchor. The second probe, designated the reporter probe, is an oligonucleotide (nucleic acid) sequence, which is complementary to a portion of the target nucleic acid sequence distinct from the sequence complementary to the capture probe and from that of the primers, to which is attached a reporter group. The capture probe and the reporter probe must be complementary to the same nucleic acid strand. The result is the formation of a sandwich containing the target nucleic acid, the capture probe, and the reporter probe.

c) The nucleic acid sandwich is then captured from solution by interaction of the anchor group on the capture probe and an anchor receptor which is attached to a solid surface. The captured sandwich is washed with appropriate buffers to remove unhybridized reporter probe.

In the so-called simultaneous assay, the single stranded nucleic acid is contacted simultaneously with both capture and reporter probes and with the solid support having the anchor receptor group attached to its surface. In this manner, the formation of the above described sandwich and its capture from solution can occur substantially simultaneously.

The presence and quantity of the reporter group on the support is then detected and/or measured and is proportional to the amount of amplified target nucleic acid. The amount of amplified target nucleic acid present, in turn, is proportional to the unamplified target nucleic acid originally present in the sample.

The simultaneous assay provides an advantage over techniques previously described in that by combining hybridization and capture into a single step, the total time requirement for the assay can be reduced by approximately 50% over methods which employ separate hybridization and capture steps. Also, the number of major manipulative steps is reduced.

It was also found surprisingly that the sensitivity of the simultaneous assay method, expected to have been reduced, was not adversely affected. Ordinarily, a capture probe having an anchor group such as a biotinylated capture probe would be expected to be removed from solution by interaction with a streptavidin (anchor receptor group)—coated solid support. Such lowered concentration of the biotinylated capture probe would be expected to reduce the sensitivity of the simultaneous assay because hybridization is a concentration-dependent reaction step. Unexpectedly, however, the simultaneous assay employing solution sandwich hybridization with simultaneous capture (immobilization) on streptavidin-coated chromium dioxide particles or microtiter plates was found to be as sensitive as assays of this invention performed utilizing sequential hybridization and immobilization steps.

The term "PCR" as used herein in referring to the process of amplifying target nucleic acid sequences employing primer oligonucleotides to produce by enzymatic means a greatly increased number of copies of a small portion of the target nucleic acid is described in U.S. Pat. No. 4,683,202.

The term capture probe as used herein refers to an oligonucleotide which is complementary to a portion of a preselected sequence of the target nucleic acid and which has attached to it a functional group referred to as an anchor. The capture probe cannot be complementary to either primer or to those portions of a primer extension product whose nucleic acid sequences are defined by the primers. The capture probe is an oligonucleotide with an attached anchor group. Anchor group attachment can be achieved, for example, by modifying an oligonucleotide at a predetermined nucleotide base such that a linker arm of at least three atoms length is added. This linker arm is capable of being attached to the anchor, which is complementary to an anchor receptor. The anchor receptor is positioned on the surface of a solid support and is used to immobilize the capture probe.

The term reporter probe as used herein refers to an oligonucleotide which is complementary to a portion of a preselected sequence of the target nucleic acid which sequence is distinct from the portion of the target nucleic acid which is complementary to the capture probe. The reporter probe cannot be complementary to either primer nor to those portions of a primer extension product whose nucleic acid sequences are defined by the primers nor to the capture probe. A reporter group is covalently attached to the oligonucleotide to form the reporter probe. This attachment can be through a linker arm as described above.

The assay of this invention requires that both the capture probe and the reporter probe be complementary to the same nucleic acid strand.

Useful reporter groups for the reporter probes of this invention include any moiety detectable subsequent to hybridization and immobilization events such as enzymes, fluorophores, chemiluminescent compounds, chromogens, and chromophores. Among enzymes are included alkaline phosphatase, horseradish peroxidase, and luciferase.

Useful anchor groups for the capture probes of this invention include any moiety capable of interacting with anchor receptor groups attached to the surface of said support to permit immobilization of the sandwich formed in the hybridization process. For example, anchors can be members of any specific immune or nonimmune binding pair such as antigen-antibody, protein A-IgG, and biotin-avidin or streptavidin.

Solution sandwich hybridization as used herein refers to a process of contacting the target nucleic acid simultaneously or sequentially, with the capture and reporter oligonucleotide probes. It is preferred that there be a simultaneous addition of a solution of both probes to a solution of the target nucleic acid.

Simultaneous assay as used herein refers to a process which employs solution sandwich hybridization with the substantially simultaneous immobilization of the formed sandwich. The process includes contacting the target nucleic acid simultaneously with capture and reporter oligonucleotide probes and with a solid support having an anchor receptor group attached to its surface. It is preferred that there be a simultaneous addition of a solution of both probes and the solid support to a solution of the target nucleic acid.

The PCR target amplification reaction requires approximately 20 to 30 repeat cycles in order to produce a sufficient quantity of the amplified target nucleic acid for further hybridization. Denaturation of the amplified nucleic acid can be accomplished by treatment with alkali, acid, chaotropic agents, or heat, although the preferred method is to place the amplified target nucleic acid in a boiling water bath for at least 10 minutes followed by a chilled water bath (4° C.) for at least two minutes.

Solution hybridization can be accomplished by contacting the single stranded target nucleic acid in solution with both capture and reporter probes, dissolved in an appropriate buffer, for a period of from 1 to 30 minutes, preferably for 10 minutes. Solution hybridization and simultaneous capture can be accomplished similarly by also adding the solid support. Preferably, both probes are used in excess. The length of the capture probe is determined by the ease of its synthesis, by the desired reaction kinetics, and by the identity of the reporter probe and the primers, and preferably is an oligonucleotide of approximately 20 to 30 nucleotide bases. The length of the reporter probe is determined by the case of its synthesis, by the desired reaction kinetics, and by the identity of the capture probe and the primers, and preferably is an oligonucleotide of approximately 20 to 30 nucleotide bases.

The capture probe—target nucleic acid—reporter probe sandwich so formed is then contacted with a solid support having an anchor receptor on its surface capable of forming a stable attachment such as a complex with the sandwich through the anchor group of the capture probe. Alternatively, the sandwich is formed in the presence of this solid support. A variety of solid supports and anchor receptors can be utilized. Among solid supports are included magnetic particles such as the chromium dioxide particles disclosed by Lau et al., U.S. Pat. No. 4,661,408, incorporated herein by reference, microtiter plates, or membranes. A preferred membrane incorporated in a device useful in carrying out the assay of this invention is described in applicants' assignee's, E. I. du Pont de Nemours and Company, copending patent application filed concurrently herewith, Ser. No. 07/192,087, filed May 10, 1988, incorporated herein by reference.

This device is an improved assay device for detecting or quantitating the presence or absence of a substance in a sample suspected or known to contain said substance, said device having multiple layers comprising: (a) a permeable membrane having a capture reagent attached thereto, (b) an intermediate layer, and (c) an absorbent layer, wherein layer (b) is in direct communication with layers (a) and (c), the improvement wherein layer (b) is a selectively permeable membrane and has at least one hole therethrough, the hole is directly below the capture reagent, and the area of said hole or the combined area of a plurality of holes is less than the area covered by the capture reagent. The term "selectively permeable" refers to materials which do not permit the substantial passage of aqueous solutions therethrough whether or not they permit the passage of other liquids such as organic solvents, if present.

Materials which can be used for the permeable layer, on which the capture reagent is spotted, include various natural or synthetic materials, which may be individual materials or combinations of materials, which may be organic, inorganic or combinations thereof. The permeable layer must be bibulous, i.e., it allows the flow of aqueous solutions therethrough without substantially impeding the movement of solutes employed in the assay. The material selected must also be one to which the capture reagent can be attached to a localized area of the device, either covalently or non-covalently, directly or indirectly as is discussed below. Exemplary materials which can find use include polysaccharides, e.g., cellulosic materials, such as paper, cellulose acetate, nitrocellulose, and backed nitrocellulose; inorganic materials, such as silica, deactivated alumina, diatomaceous earth, $MgSO_4$ or other inorganic finely divided material substantially uniformly dispersed in a porous polymer matrix, with polymers such as vinyl chloride, vinyl chloride-propylene copolymer, and vinyl chloride-vinyl acetate copolymer; cloth, both naturally occurring, e.g., cotton, and synthetic, e.g., nylon cloth; porous gels, e.g., silica gel, agarose, dextran, and gelatin; polymeric films, e.g., polyacrylamide and the like.

There can also be mentioned, in particular, membranes to which proteins can be covalently attached. The list includes the following which can be purchased commercially: microporous affinity membranes with a pore size in the range of about 0.5 to about 5 micrometers, membranes with a chemically preactivated surface which offer a high density of covalent binding sites that immobilize proteins on contact, and chemically activated hydrophilic microporous membranes wherein the base membrane is hydrophilic polyvinylidene fluoride, chemically derivatized to allow protein immobilization through epsilon amino groups of lysine or arginine in the pH range of 7 to 9. For a sensitive assay, the choice of membrane depends primarily upon the ability to prevent nonspecific binding on the membrane by blocking it. This in turn depends upon the reagents selected, the blocking agent, and the membrane itself. The preferred membrane in practicing the invention is a chemically activated hydrophilic microporous membrane.

The selectively permeable layer of this multi-layer device prevents the flow of aqueous solutions under the assay conditions. This resistance to flow is important because it increases the amount of time the capture reagent contacts the other reagents used in the assay, thus improving subsequent steps in building the sandwich and assaying the enzyme, as well as the overall sensitivity of the assay. A wide variety of compositions of known flow characteristics can be used for the selectively permeable layer which includes polyethylene, polyethylene-backed polytetrafluoroethylene and fibrous-porous polytetrafluoroethylene. A fibrous-porous polytetrafluoroethylene membrane is the preferred material for the selectively permeable layer in practicing the instant invention. The fibrous-porous nature of the membrane appears to encourage radial flow along the surface so that liquid flows to the center where the holes are located in the selectively permeable layer. During the assay, no aqueous reagents pass through the pores in the fibrous-porous polytetrafluoroethylene membrane, which is selectively permeable with respect to the aqueous assay reagents.

The absorbent layer serves as a repository for excess reagent solutions. Consequently, all the reactants needed to produce color are present in the absorbent layer. Since development of color in the absorbent layer is not desirable, a variety of reagents can be added to the absorbent layer to reduce production of background color in the absorbent layer. According to the present invention, surprisingly and unexpectedly it has been found that when an enzyme-based detection system is used, color development in the absorbent layer can be minimized by saturation with a solution containing an enzyme inhibitor specific for the enzyme selected to detect.

To remove non-hybridized reporter probe, the immobilized sandwich can then be washed several times, for example, in the temperature range of 25° C.–37° C., for approximately 5 to 10 minutes per wash cycle.

A variety of known detection methods can be utilized in the assay of this invention depending on the type of the reporter groups present on the reporter probes. In general, when the reporter group is an enzyme, a substrate or substrates specific for that enzyme is used along with all other necessary reagents. Color formation can then be detected and/or measured photometrically. When the reporter group is the enzyme alkaline phosphatase, then the preferred substrates are 4-methylumbelliferyl phosphate or p-nitrophenyl phosphate when the solid support is a magnetic particle or a microtiter plate, and the combination of nitro-blue tetrazolium (NBT) and 5-bromo-4-chloro-3-indolyl phosphate (BCIP) when the solid support is the modified membrane described above.

It has been found unexpectedly that when the assay of this invention is carried out, the sensitivity of such an assay is significantly improved over previous DNA probe assay processes. When PCR methodology was combined with a direct hybridization assay ("dot blot"), 1,000 copies of HIV I DNA could be detected using chromogenic detection. Since such a direct assay is known to be more sensitive than the solution sandwich assay, it was particularly surprising to find that the solution sandwich assay format on a membrane device, when combined with the PCR methodology in the assay of this invention, again using chromogenic detection, detected 100 copies of HIV I DNA, a 10-fold improvement. When the assay of this invention utilized fluorescent detection, irrespective of the type of solid support, there was also found an increased detection level to 100 copies of HIV I DNA. Furthermore, fluorescent detection methodology cannot be utilized with the direct (dot blot) assay, which is thus limited to a less sensitive detection limit.

To appreciate the sensitivity of the nucleic acid probe assay of this invention, it has to be noted that the absolute sensitivity, as indicated by using only 5% of the amplified target DNA produced by the PCR portion of the assay process, was equal to 5 copies of unamplified starting HIV I DNA. Such results were obtained using the membrane device of this invention, with fluorescent detection combined with the streptavidin-coated microtiter plate or streptavidin coated chromium dioxide particles. This level of sensitivity represents a hitherto unachievable goal with this type of assay.

The Examples below exemplify the invention.

EXAMPLE I

Detection of HIV I

A. Amplification of Target Nucleic Acid by PCR

The procedure as described in U.S. Pat. No. 4,683,202 and in a product bulletin for GeneAmp DNA Amplification Reagent Kit (#N801-0043) was followed utilizing the following specific conditions and reagents. A 103-nucleotide base sequence located within the GAG p17 region of HIV I, incorporated into a plasmid (the plasmid incorporating most of the HIV I genome is designated pBH10-R3), was amplified using primers A and B as shown below:

5'-TGGGCAAGCAGGGAGCTAGG
Primer A

5'-TCTGAAGGGATGGTTGTAGC
Primer B

Aliquots of serial dilutions ($1 \times 10^{+7}$, $1 \times 10^{+6}$, $1 \times 10^{+5}$, $1 \times 10^{+4}$, $1 \times 10^{+3}$, $1 \times 10^{+2}$, $1 \times 10^{+1}$, and zero copies) of plasmid pBH10-R3 were amplified using PCR. Each aliquot was combined with a buffer which was 200 $\mu$m in each of dATP, dTTP, dCTP, and dGTP, 1.0 $\mu$m in each of Primer A and Primer B, and contained 1 $\mu$g of human placental DNA/reaction and 2.5 units of TAQ polymerase, in a total reaction volume of 100 $\mu$l.

Each reaction mixture was then temperature cycled as described in the product bulletin thirty (30) times.

This process resulted in the estimated increase in the number of target molecules of $1 \times 10^{+5}$ to $1 \times 10^{+6}$.

B. Solution Sandwich Hybridization

1) Denaturation:

10 $\mu$l of amplified target DNA from each of the above aliquots was combined with 30 $\mu$l of H$_2$O in a 1.5-ml Eppendorf tube and placed in a boiling water bath for 10 minutes. The tubes were then transferred to a chilled water bath (4° C.) for two minutes and then centrifuged in a microcentrifuge for 10 seconds.

2) Hybridization:

The denatured samples were split into two 20-$\mu$l portions (in Eppendorf tubes) in order that duplicate samples could be run. 100 $\mu$l of hybridization mix that had been pre-equilibrated at 37° C. for 10 minutes was added. Hybridization mix (HM) was prepared by combining 1987 $\mu$l of hybridization buffer, 12.4 $\mu$l of alkaline phosphatase-labeled reporter probe ($6.2 \times 10^{-12}$ moles), 1.5 $\mu$l of biotinylated capture probe ($4.5 \times 10^{-11}$ moles), and 40 $\mu$l of a 50 mg/ml solution of bovine serum albumin (BSA). The sequences of the probes are shown below. Hybridization buffer (HB) was prepared by combining: 3 ml of 20× SSC, pH 7.0, 0.1 ml of Triton X-100, an alkylaryl polyether alcohol having 9–10 ethoxy units, 1.0 ml of deionized formamide, 6.375 ml of H$_2$O, and 25 $\mu$l of 1.0N HCl. The samples were hybridized for 10 minutes at 30° C.

5'-CCCAGTATTTGTCTACAGCCTTCTG
Reporter Probe

5'-CAGGCCAGGATTAACTGCGAATCGT
Capture Probe

C. Immobilization and Detection

Hybridized sample solutions prepared as described above were immobilized using three different solid supports: streptavidin-coated chromium dioxide particles, streptavidin coated microtiter plates, and streptavidin coated membranes as described above.

1) Immobilization and Detection on Streptavidin Coated Chromium Dioxide Particles:

120 $\mu$l aliquots of solution sandwich hybridization mixtures of each target nucleic acid amplification dilution levels were added to 12 $\mu$l of streptavidin-coated chromium dioxide particles (12 $\mu$g), prepared as described in U.S. Pat. No. 4,661,408). The samples were then incubated for 10 minutes at 37° C., centrifuged in a microfuge for 5 seconds, and placed in a Corning magnetic rack for two minutes at 25° C. The pellets were washed twice at 25° C. by adding 200 $\mu$l of wash buffer (WB) containing 1× SSC, pH 7.0 and 0.17% Triton X-100, mixing, placing the samples in a magnetic rack for 2 minutes, and removing the wash buffer. The samples were washed a third time as described above except that they were incubated for 5 minutes at 37° C. prior to placing them in the magnetic rack.

Detection was accomplished by adding 50 $\mu$l of an alkaline phosphatase substrate solution to each sample containing 1M diethanolamine, pH 8.9, 5 mM MgCl$_2$, 2 mM zinc acetate, 2 mM N-(2-hydroxy-ethyl)ethylenediaminetriacetic acid (HEDTA), and 200 $\mu$M 4-methylumbelliferyl phosphate and 200 $\mu$M p-nitrophenyl phosphate, for fluorescence and chromogenic detection, respectively. The samples were incubated for 2 hours at 37° C. For fluorescence detection, 10 $\mu$l of each sample was diluted with 390 $\mu$l of water. The fluorescence signal generated for each sample was measured in a SPEX F212 spectrofluorometer by exciting at 365 nm and measuring the emitted fluorescence at 450 nm. For chromogenic detection, p-nitrophenol was detected by measuring the absorbance of the samples at 405 nm.

2) Immobilization and Detection on Streptavidin Coated Microtiter Plates

Streptavidin was coated onto microtiter plates as follows: 100 $\mu$l of a 10 $\mu$g/ml solution of streptavidin prepared in a 0.1M sodium carbonate buffer, pH 9.6, was added to each well of a micro-titer plate and allowed to bind overnight (16 hours) at 4° C. The wells were then washed three times at 25° C. in a wash buffer which was 15 mM in sodium citrate, 150 mM in sodium chloride, and contained 0.17% Triton X-100. The wells were then blocked by adding 300 $\mu$l of 1× phosphate buffered saline (PBS), pH 7.4, containing 2% bovine serum albumin (BSA) and 0.01% thimerosal, and incubated for 2 hours at 37° C. The microtiter plates were stored in this buffer at 4° C. until needed, at which time they were washed once at 25° C. in wash buffer.

100 $\mu$l of the solution sandwich hybridization mixture for each target nucleic amplification level was added to individual wells in the microtiter plate and incubated at 37° C. for one hour. Each well was then washed three times with wash buffer at 25° C. 100 $\mu$l of substrate buffer (as described above) containing either 4-methylumbelliferyl phosphate or p-nitrophenyl phosphate, was added to each well of the microtiter plate. The plate was incubated at 37° C. Fluorescence due to the formation of 4-methylumbelliferone was measured as described above after 3 hours and the presence of p-nitrophenol was detected by measuring the absorbance of the samples at 405 nm after 2.5 hours in a spectrophotometer.

3) Immobilization and Detection in a Membrane Device

Membrane devices were prepared as described in applicants' assignee's copending application, see above. For the purpose of this assay, 50 μg of streptavidin in a 2 μl volume containing 1× PBS was spotted onto the permeable top membrane of the device. The membranes were dried at 37° C. for 5 minutes. 500 μl of 5% fish gelatin in 1× PBS was then added to each membrane and incubated overnight at 37° C. The devices were then assembled as described in applicants' assignee's copending application, see above. For Immobilization, 100 μl of the solution sandwich hybridization mixture for each target nucleic amplification level was diluted to 400 μl with Herptran ™ and added to individual membrane devices, which were allowed to stand at 25° C. for 10 minutes. Wash buffer (200 μl of 0.1M Tris, pH 9.5, containing 0.05% Tween ® 20) was added and allowed to flow through the devices. 200 μl of substrate solution (0.1M Tris, pH 9.6, containing BCIP/NBT as described in applicants' assignee's copending application) was then added to each device which were then incubated for 10 minutes at 25° C. Another 200 μl of substrate solution was then added to each sample which were allowed to incubate for another 10 minutes at 25° C. 200 μl of stop solution (1.0N HCl) was added to each sample. The presence of colored spots in the center of the membranes was indicative of a positive response.

EXAMPLE II

Detection of HIV I DNA—Comparative Example

A. Immobilization of Amplified Target DNA

The amplified target DNA from each of the aliquots in Example I was Immobilized on GENE SCREEN ™ hybridization membrane by first denaturing 5 μl of each dilution reaction in 95 μl of 0.2N sodium hydroxide at room temperature for one min. and then filtering the reactions products through the membrane using a dot blot device. The DNA resulting from the PCR process is then retained on the GENE SCREEN surface. The wells of the dot blot device were then rinsed with 200 μl of 5× SSC. The membrane was then removed from the dot blot device and exposed to ultraviolet light at 302 nm for five minutes, which linked the PCR products to the membrane surface.

Hybridization between the immobilized PCR products and the reporter probe utilized in Example I was then carried out in a sealable pouch. This was performed by first prehybridizing the membrane with the immobilized PCR products for 10 minutes at 50° C. in 1 ml of a buffer containing 5× SSC, 0.5% bovine serum albumin, 0.5% polyvinylpyrrolidone, and 1% SDS, and then adding the alkaline phosphatase labeled reporter probe to the hybridization pouch at a final concentration of 2.5 nM. The membrane was hybridized for 15 minutes at 50° C. The membrane was removed from the sealable pouch and washed twice by agitating the membrane in a solution of 250 ml 1× SSC, containing 1% SDS for 5 minutes at 45° C. in order to remove any unhybridized probe. The membrane was further washed twice by agitating the membrane in 250 mL of 1× SSC, containing 1% Triton X-100, at 45° C. for five minutes. Finally, the membrane was washed once agitating in 250 ml of 1× SSC at room temperature for 5 minutes.

B. Detection

The hybridized probe was detected by placing the membrane in 8 mL of development buffer (10 μM Tris, pH 9.6, containing 50 mM NaCl, 10 μM MgCl₂, and 10 μm of each of NBT and BCIP). The reaction was incubated at 37° C. for 30 minutes. Probe hybridized to the PCR reaction products was visualized on the membrane by the deposition of dye resulting from the alkaline phosphatase activity of the probe.

The results of this experiment and the data from Example I utilizing the assay of this invention are summarized in Table I. The use of the solution sandwich assay in conjunction with PCR, the assay of this invention, results in surprisingly greater sensitivity than does combining the PCR amplification method with the dot blot assay method. In the dot blot direct assay method, background of nonspecific origin obscured the detection below the 1000 copy level of pre-amplified pBH10-R3 target DNA.

TABLE I

| ASSAY TYPE | ASSAY SENSITIVITY COPIES DETECTED | | PCR CYCLES | TIME |
|---|---|---|---|---|
| | CHROM. | FLUOR. | | |
| DIRECT - [DOT BLOT] | 1000 | — | 30 | 6 hr. |
| THIS INVENTION | | | | |
| MAGNETIC PARTICLE | 1000 (50) | 100 (5) | 20 | 5 hr. |
| MICROTITER PLATE | 1000 (50) | 100 (5) | 30 | 6 hr. |
| MEMBRANE DEVICE | 100 (5) | — | 30 | 5 hr. |

Note:
The values in parentheses indicate the approximate levels of sensitivity as indicated by the fact that only 5% of the amplification reaction volumes was used for each assay point in each assay format and immobilization/detection method.

EXAMPLE III

Detection of HIV I—Simultaneous Assay

A. Amplification of Target Nucleic Acid by PCR

The procedure as described in U.S. Pat. No. 4,683,202 and in a product bulletin for GeneAmp DNA Amplification Reagent Kit (#N801-0043) was followed utilizing the following specific conditions and reagents. A 103-nucleotide base sequence located within the GAG p17 region of HIV I, incorporated into a plasmid (the plasmid incorporating most of the HIV I genome is designated pBH10-R3), was amplified using primers A and B as shown below:

5'-TGGGCAAGCAGGGAGCTAGG
Primer A
5'-TCTGAAGGGATGGTTGTAGC
Primer B

Aliquots of serial dilutions ($1\times10^{+7}$, $1\times10^{+6}$, $1\times10^{+5}$, $1\times10^{+4}$, $1\times10^{+3}$, $1\times10^{+2}$, $1\times10^{+1}$, and zero copies) of plasmid pBH10-R3 were amplified using PCR. Each aliquot was combined with a buffer which was 200 μM in each of dATP, dTTP, dCTP, and dGTP, 1.0 μM in each of Primer A and Primer B, and contained 1 μg of human placental DNA/reaction and 2.5 units of TAQ polymerase, in a total reaction volume of 100 μl.

Each reaction mixture was then temperature cycled as described in the product bulletin thirty (30) times.

This process resulted in the estimated increase in the number of target molecules of $1 \times 10^{+5}$ to $1 \times 10^{+6}$.

B. Denaturation

10 μl of amplified target DNA from each of the above aliquots was combined with 30 μl of H₂O in a 1.5-ml Eppendorf tube and placed in a boiling water bath for 10 minutes. The tubes were then transferred to a chilled water bath (4° C.) for two minutes and then centrifuged in a microcentrifuge for 10 seconds.

C. Simultaneous Hybridization and Capture

1) Simultaneous Hybridization and Capture on Streptavidin-Coated Chromium Dioxide Particles 20-μl portions of denatured material prepared as described above were combined in Eppendorf tubes with 12 μl of streptavidin-coated chromium dioxide particles and 100 μl of hybridization mix that had been pre-equilibrated at 37° C. for 10 minutes. Hybridization mix (HM) was prepared by combining 1987 μl of hybridization buffer, 12.4 μl of alkaline phosphatase-labeled reporter probe ($6.2 \times 10^{31\ 12}$ moles), 1.5 μl of biotinylated capture probe ($4.5 \times 10^{31\ 11}$ moles), and 40 μl of a 50 mg/ml solution of bovine serum albumin (BSA). The sequences of the probes are shown below:

5'-CCCAGTATTTGTCTACAGCCTTCTG
Reporter Probe
5'-CAGGCCAGGATTAACTGCGAATCGT
Capture Probe Hybridization buffer (HB) was prepared by combining: 3 ml of 20× SSC, pH 7.0, 0.1 ml of Triton X-100, an alkylaryl polyether alcohol having 9–10 ethoxy units, 1.0 ml of deionized formamide, 6.375 ml of H₂O, and 25 μl of 1.0N HCl. The samples were hybridized for 10 minutes at 37° C., centrifuged in a microfuge for 5 seconds, and placed in a Corning magnetic rack for two minutes at 25° C. The pellets were washed twice at 25° C. by adding 200 μl of wash buffer (WB) containing 1× SSC, pH 7.0 and 0.17% Triton X-100, mixing, placing the samples in a magnetic rack for 2 minutes, and removing the wash buffer. The samples were washed a third time as described above except that they were incubated for 5 minutes at 37° C. prior to placing them in the magnetic rack.

Detection was accomplished by adding 50 μl of an alkaline phosphatase substrate solution to each sample containing 1M diethanolamine, pH 8.9, 5 mM MgCl₂, 2 mM zinc acetate, 2 mM N-(2-hydroxy-ethyl)ethylenediaminetriacetic acid (HEDTA), and 200 μM 4-methylumbelliferyl phosphate and 200 μM p-nitrophenyl phosphate, for fluorescence and chromogenic detection, respectively. The samples were incubated for 2 hours at 37° C. For fluorescence detection, 10 μl of each sample was diluted with 390 μl of water. The fluorescence signal generated for each sample was measured in a SPEX F212 spectrofluorometer by exciting at 365 nm and measuring the emitted fluorescence at 450 nm. For chromogenic detection, p-nitrophenol was detected by measuring the absorbance of the samples at 405 nm.

2) Simultaneous Hybridization and Capture on Streptavidin Coated Microtiter Plates Streptavidin was coated onto microtiter plates as follows: 100 μl of a 10 μg/ml solution of streptavidin prepared in a 0.1M sodium carbonate buffer, pH 9.6, was added to each well of a micro-titer plate and allowed to bind overnight (16 hours) at 4° C. The wells were then washed three times at 25° C. in a wash buffer which was 15 mM in sodium citrate, 150 mM in sodium chloride, and contained 0.17% Triton X-100. The wells were then blocked by adding 300 μl of 1× phosphate buffered saline (PBS), pH 7.4, containing 2% bovine serum albumin (BSA) and 0.01% thimerosal, and incubated for 2 hours at 37° C. The microtiter plates were stored in this buffer at 4° C. until needed, at which time they were washed once at 25° C. in wash buffer.

20-μl portions of denatured sample were combined in streptavidin-coated microtiter plate wells with 100 μl of the solution sandwich hybridization mixture and incubated at 37° C. for one hour. Each well was then washed three times with wash buffer at 25° C. 100 μl of substrate buffer (as described above) containing either 4-methylumbelliferyl phosphate or p-nitrophenyl phosphate, was added to each well of the microtiter plate. The plate was incubated at 37° C. Fluorescence due to the formation of 4-methylumbelliferone was measured as described above after 3 hours or the presence of p-nitrophenol was detected by measuring the absorbance of the samples at 405 nm after 2.5 hours in a spectrophotometer.

What is claimed is:

1. A nucleic acid probe assay for the detection and/or measurement of a preselected target nucleic acid sequence in a sample comprising the steps of:
   (A) rendering the target nucleic acid single-stranded;
   (B) amplifying at least one specific nucleic acid sequence contained within the preselected nucleic acid sequence by
      (1) treating the strands with two oligonucleotide primers, for each different specific sequence being amplified, under conditions such that for each different sequence being amplified an extension product of each primer is synthesized which is complementary to each nucleic acid strand, wherein said primers are selected so as to be sufficiently complementary to the different strands of each specific sequence to hybridize therewith such that the extension product synthesized from one primer, when it is separated from its complement, can serve as a template for synthesis of the extension product of the other primer;
      (2) separating the primer extension products from the templates on which they were synthesized to produce single-stranded molecules; and
      (3) treating the single-stranded molecules generated from step (2) with the primers of step (1) under conditions that a primer extension product is synthesized using each of the single strands produced in step (2) as a template;
      (4) repeating steps (2) and (3) to produce sufficient primer extension product for detection and/or measurement;
   (C) rendering the product or products of step (B)(4) single-stranded;
   (D) contacting the product or products of step (C) simultaneously with capture and reporter probes in solution and with a solid support having an anchor receptor group on its surface; wherein said capture probe is complementary to a portion of a primer extension product not including the nucleic acid sequences defined by both primers; wherein said reporter probe is complementary to a portion of a primer extension product not including the nucleic acid sequences defined by the capture probe and by both primers; wherein the capture and reporter probes are complementary to the same nucleic acid strand; and wherein the anchor receptor group on the surface of the solid support is capable of interacting with the anchor group of the capture probe leading to the immobilization of the sandwich product formed in this step;

(E) removing any unhybridized reporter probe; and (F) detecting and/or measuring the reporter group or reporter groups immobilized on the solid support, wherein said detection and/or measurement is directly correlated to the detection and/or measurement of said target nucleic acid sequence.

* * * * *